United States Patent [19]
Boese

[11] Patent Number: 5,195,983
[45] Date of Patent: Mar. 23, 1993

[54] SYRINGE GUARD AND DISPOSAL SYSTEM

[75] Inventor: Ted Boese, Loxahatchee, Fla.

[73] Assignee: Penta Associates, Loxahatchee, Fla.

[21] Appl. No.: 750,822

[22] Filed: Aug. 27, 1991

[51] Int. Cl.[5] ............................................ A61M 5/32
[52] U.S. Cl. ................................... 604/192; 604/198; 604/110
[58] Field of Search ............... 604/110, 192, 198, 263, 604/187, 218; 128/919

[56] References Cited

U.S. PATENT DOCUMENTS

| | | |
|---|---|---|
| 4,664,654 | 5/1987 | Strauss .................. 604/198 |
| 4,795,432 | 1/1989 | Karczmer .............. 604/110 |
| 4,850,996 | 7/1989 | Cree ....................... 604/198 |
| 4,863,435 | 9/1989 | Sturman et al. ...... 604/198 |
| 4,887,998 | 12/1989 | Martin et al. ......... 604/110 |
| 4,894,055 | 1/1990 | Sudnak .................. 604/198 |
| 4,900,311 | 2/1990 | Stern et al. ........... 604/198 |
| 4,911,693 | 3/1990 | Paris ...................... 604/192 |
| 4,917,672 | 4/1990 | Terndrup et al. .... 604/192 |
| 4,921,490 | 5/1990 | Spier et al. ........... 604/192 |
| 4,932,940 | 6/1990 | Walker et al. ........ 604/110 |
| 4,935,012 | 6/1990 | Magre et al. ......... 604/192 |
| 4,955,866 | 9/1990 | Corey .................... 604/192 |
| 5,059,181 | 10/1991 | McLees ................. 604/110 |
| 5,135,502 | 8/1992 | Koenig et al. ........ 604/164 |
| 5,135,505 | 8/1992 | Kaufman ............... 604/165 |
| 5,135,510 | 8/1992 | Maszkiewicz et al. .. 604/195 |

FOREIGN PATENT DOCUMENTS

| | | | |
|---|---|---|---|
| 0409180 | 1/1991 | European Pat. Off. ......... 604/192 |
| 9000075 | 1/1990 | PCT Int'l Appl. ............... 604/198 |
| 9003815 | 4/1990 | PCT Int'l Appl. ............... 128/919 |
| 9008564 | 8/1990 | PCT Int'l Appl. ............... 604/192 |

*Primary Examiner*—C. Fred Rosenbaum
*Assistant Examiner*—Mark O. Polutta
*Attorney, Agent, or Firm*—Quarles & Brady

[57] ABSTRACT

Apparatus for the safe use and disposal of a syringe includes a needle guard for covering the needle of the syringe. The needle guard is slidable between retracted and extended positions. Biasing structure is adapted to urge the needle guard over the needle. The needle guard slides to the retracted position, in opposition to the biasing structure, for injecting a subject, and slides over the needle as it is withdrawn from a subject in response to the biasing structure. Structure for locking the needle guard in the fully extended position upon complete withdrawal of the needle from the subject is also provided. A cam member is preferably provided with cam surfaces and engagement portions which co-operate with cam control surfaces to effect retention of the cam member in a retracted position during a filling operation, and locking of the needle guard over the needle for disposal.

7 Claims, 7 Drawing Sheets

SYRINGE GUARD AND DISPOSAL SYSTEM

FIELD OF THE INVENTION

This invention relates to the field of medical devices and more specifically to an improved apparatus for protecting and disposing of the needle portion of a syringe.

BACKGROUND OF THE INVENTION

Syringes are a well-known means of injecting fluids into or removing fluids from living subjects such as humans and animals. Recently, great concern has arisen over the use of these devices due to the potential contamination or infection of medical personnel treating patients with communicable diseases through the accidental puncture of the skin of treating personnel and the resulting transfer of contaminated or infectious fluids.

A variety of systems and devices have been developed for protecting against the potential hazards to medical personnel posed by unprotected syringes. For example, in U.S. Pat. No. 4,477,998 an apparatus is disclosed wherein a spring-loaded mechanism is deployed which advances a protective sheath towards the tip of a hypodermic needle. As the needle is withdrawn, the protective sheath advances beyond the tip of the needle where a movable ball-bearing slides over the tip of the needle to provide a positive locking mechanism which irreversibly encapsulates the tip of the needle. In a system disclosed in U.S. Pat. No. 4,894,055, a needle guard assembly is disclosed wherein a plurality of telescoping concentric members comprising a needle guard are moved into a locking position by a spring biasing member such that movable tabs on an inner member engage a cooperating detent on the inner surface of an outer member to lock the inner member in an extended position. U.S. Pat. No. 4,911,693 also discloses a needle guard assembly having a plurality of telescoping concentric members wherein a first member is fixedly mounted to a syringe body. A second member is movably mounted within the first member and is movable between a first position wherein the needle is unexposed and a second position wherein the needle is exposed. Means are provided for urging the second member towards the first position and means are also provided for permanently locking the second member in a position wherein the needle tip is unexposed. However, in this system, the needle guard is not locked automatically. Specifically, the needle guard portion of the syringe incorporates a tab which engages a "T" shaped groove in the first member. To utilize the syringe, the needle guard is manually rotated 90 degrees to move the tab to a longitudinal groove which allows the tab and needle guard to move to a retracted position for injections. When the injection is complete, the needle guard must be again rotated 90 degrees so the tab engages a transverse portion of the groove to lock the needle guard in the extended position. Numerous other types of needle guard devices are known in the art such as the devices disclosed in U.S. Pat. Nos. 4,935,016, 4,938,745, 4,850,996, 4,664,654, and 4,804,371. All of the above-referenced patents are incorporated herein by reference.

While each of the above-mentioned patents describe needle guard devices which may function satisfactorily, no device is known which provides automatic, positive and fail-safe performance while simultaneously providing a device which is easily manufactured, utilizes a minimum of moving parts, which provides minimal interference when the syringe is used on a patient, and which is highly distinctive and recognizable as containing a potentially hazardous substance.

SUMMARY AND OBJECTS OF THE INVENTION

Briefly described, the present invention contemplates an apparatus for the safe use and disposal of syringes, comprising a housing having side walls and first and second end walls, wherein a plurality of the side walls include cam control surfaces disposed on an interior surface thereof. The first end wall includes means for receiving a syringe having a needle and the second end wall includes an aperture aligned with the means for receiving. A needle guard is slidably disposed through the aperture of the second end wall, between extended and retracted positions. The needle guard includes a longitudinal channel for receiving the needle and further includes a disk-like flange for limiting the movement of the needle guard with respect to the housing.

A rotable cam disposed within the housing, includes a plurality of cam arms responsive to the cam control surfaces, and includes a first and second pair of cam surfaces, wherein the first pair of cam surfaces is cooperatively disposed with respect to the disk-like flange. A spacer member is slidably disposed within the housing and includes a plurality of notches aligned with the cam control surfaces which permit the movement of the spacer member over the cam control surfaces, wherein the spacer member disposed in cooperative engagement with the second pair of cam surfaces. A spring biasing means is disposed within said housing for urging the spacer member and the cam in a direction opposing the means for receiving.

The cam control surfaces include an upwardly directed ramp surface and a resting shoulder disposed along one of the side walls and a downwardly directed ramp surface and a trigger shoulder, disposed along an opposing side wall.

The cam member is movable between initial, injecting, withdrawing and locked positions wherein in the initial position, the cam control arms engage the upwardly directed ramp surface and the trigger shoulder so that the needle guard is slidable to expose the needle for filling the syringe. In the injecting position, the cam arms are released from the upwardly directed ramp surface and the trigger shoulder to compress the first and second pair of cam surfaces between the spacer member and the disk-like flange, to permit the needle guard to slide inwardly within the housing. In the withdrawing position, the cam member moves outwardly within the housing to force the needle guard over the needle as it is withdrawn in response to forces generated by the spring. Finally, in the locked position, the cam control arms engage the downwardly directed ramp surface and the resting shoulder to lock the needle guard in a fully extended position wherein the needle is completely encased within the longitudinal channel of the locked needle guard.

Accordingly, it is an object of the present invention to provide an improved method and apparatus for the safe use and disposal of syringes.

It is another object of the invention to provide an improved apparatus for the safe use and disposal of syringes which may be manufactured with a minimum of moving parts.

It is still another object of the present invention to provide an apparatus for the safe use and disposal of syringes which is highly distinctive and recognizable.

It is still another object of the present invention to provide an apparatus for the safe use and disposal of syringes which can be easily manufactured for a low cost and from readily available materials.

BRIEF DESCRIPTION OF THE DRAWINGS

These and other objects will be readily apparent to persons of ordinary skill through the detailed description of the invention below and the accompanying drawings in which.

DETAILED DESCRIPTION OF THE PREFERRED EMBODIMENT

Figure 1:
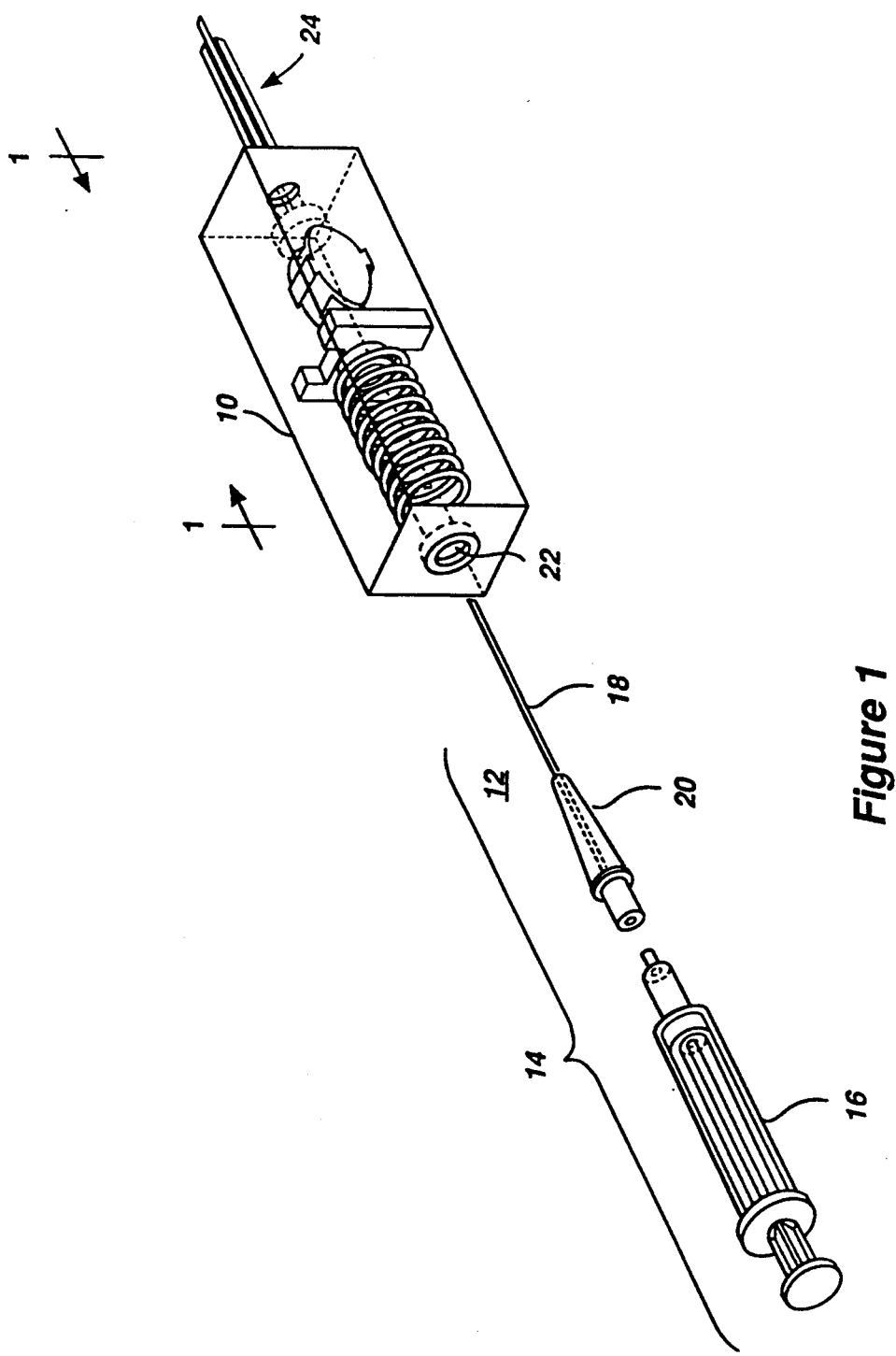
FIG. 1 is a view in perspective of the apparatus of the present invention shown in association with a conventional syringe.

The present invention provides a fail-safe guard for a syringe such as the syringe 14 shown in FIG. 1. The apparatus 10 is adapted for attachment to the needle assembly 12 of the syringe 14. The syringe 14 may be of the conventional type, comprising a conventional glass, plastic, or stainless steel injection barrel 16 and a disposable needle assembly 12. In the alternative, the syringe 14 may comprise a conventional one piece disposable unit. Typically, the needle assembly 12 includes a needle 18 and a tapered support shaft 20.

The apparatus 10 is adapted to be attached to the needle assembly 12 such that the tapered shaft 20 frictionally engages a cooperating cavity 22 disposed at one end of apparatus 10. When apparatus 10 is attached to the needle assembly 12, the needle is extends through the apparatus 10 in sliding engagement through the bore of a needle guard 24. The needle guard 24 is disposed in movable relation within apparatus 10 to accommodate the filling of injection barrel 16 and injection of the patient, and is further adapted to slide and lock in an extended position, fully covering and protecting the needle 18, after the syringe 14 has been used.

A variety of means may be utilized to attach the apparatus 10 to the needle assembly 12. In the preferred embodiment of the present invention, a simple frictional engagement may be used. Those skilled in the art will readily appreciate that cavity 22 may be configured to accommodate needle assemblies having a wide variety of dimensions and sizes, or in the alternative, may be manufactured in specific sizes to accommodate unique sizes of needle assemblies. In the alternative, the cavity 22 and tapered support shaft 20 may be configured with a complementary, intergaging, locking structure such as ribs to provide a positive locking arrangement. In yet another embodiment, the apparatus 10 and the needle assembly 12 may be formed as a single unit.

Figure 2:
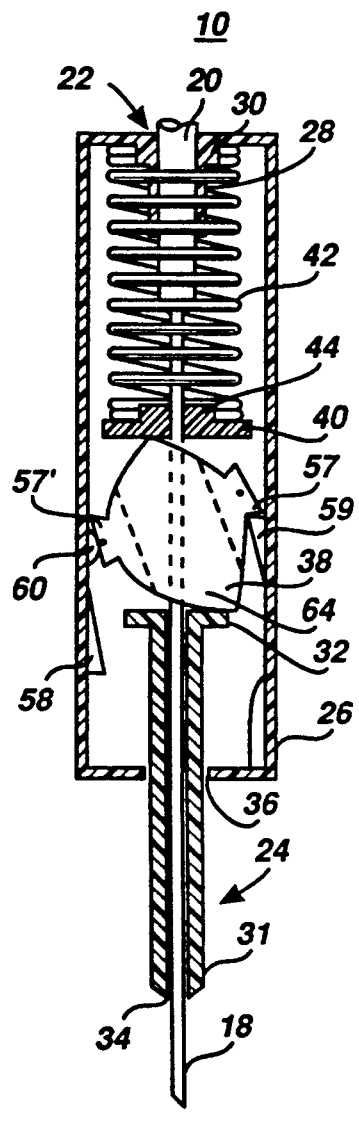
FIG. 2 is a cross-sectional view taken along section A-A' showing the apparatus of the present invention in its initial shipping and storage position.

Referring now to FIG. 2, the apparatus 10 is shown in its initial unused state. The apparatus 10 incorporates a housing 26 which preferably has a square or rectangular cross-section to distinctively identify the apparatus 10. The cavity 22 is formed in one end of housing 10 with an inwardly extending cylindrical wall 28 having an inner surface which substantially complements the outside taper of support shaft 20. The cylindrical wall 28 further includes a stepped portion 30 whose purpose and function is further discussed below. The needle guard 24 comprises a protective shaft 31 which is terminated by a disk-shaped flange 32 disposed within housing 26. The protective shaft 31 includes a longitudinal bore 34 adapted to receive needle 18. The needle guard 24 is adapted to slide within housing 26, between retracted and extended positions, along an axis defined by needle 18. The needle guard 24 extends through an orifice 36 which is aligned with cavity 22. The movement of the needle guard 24 in the extended position is limited by the disk-shaped flange 32, which abuts an end wall 37 of housing 26.

The apparatus 10 further includes a spring-biased spacer 40 which generally urges cam member 38 toward the end wall 37. A spring 42 can be attached to the stepped portion 30 of cylindrical wall 28 at one end, and to a retaining post 44 of spacer 40 at an opposite end.

Figure 5:
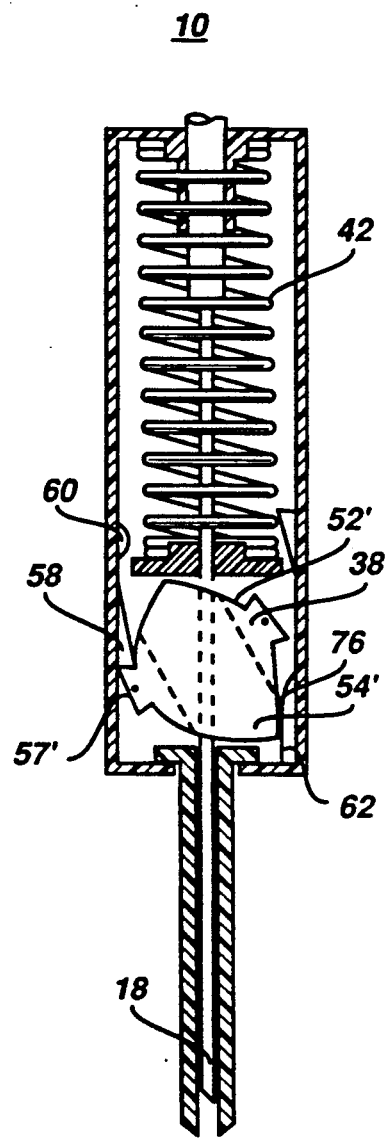
FIG. 5 is a cross-sectional view taken along section A-A', wherein the needle guard is positioned in a permanently locked position.
Figure 6:
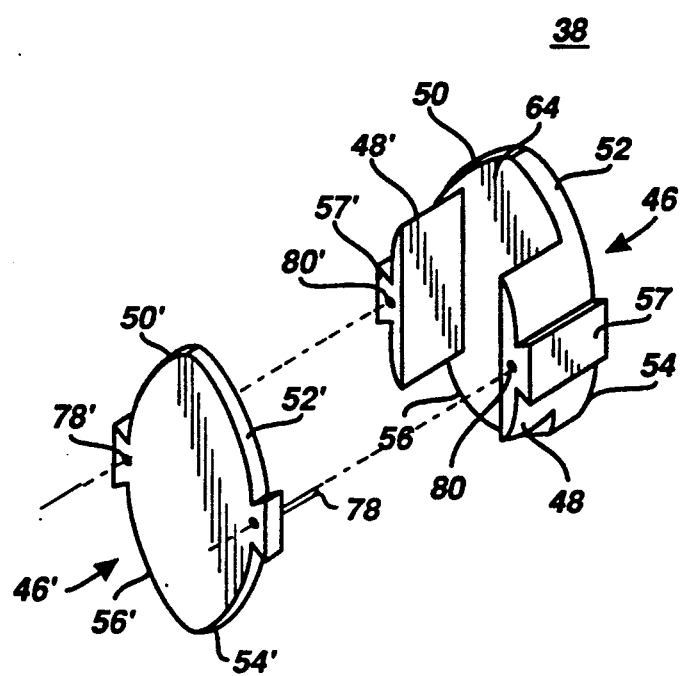
FIG. 6 is a view in perspective of the cam assembly shown in cross-sectional form in FIGS. 2-5.

As most clearly seen in FIG. 6, the cam member 38 can be fabricated with outer cam plates 46-46', which are separated by spacer walls 48-48'. The cam plates 46-46' are configured with complementary curvilinear cam surfaces 50-50', 52-52', 54-54' and 56-56', which cam surfaces cooperate with spacer 40 and disk-shaped base 32. The cam 38 further includes cam control arms 57-57' which cooperate with cam control surfaces disposed along the inner walls of housing 26, to control and define the movement of cam 38 within housing 26. The cam control surfaces are defined by a downwardly extending ramp member 58, an upwardly extending ramp member 59, a trigger shoulder 60 and a resting shoulder 62. The cam plates 50-50' and spacer walls 48-48' define an internal cavity 64 through which the needle 18 extends, as is most clearly seen in FIGS. 2-5.

In FIG. 2, the apparatus 10 is shown in an initial storage and shipping position. In this state, the cam 38 is oriented with cam control arm 57 resting against ramp member 59 and with cam control arm 57' frictionally engaging trigger shoulder 60. In this state, the frictional force between trigger shoulder 60 and cam control arm 57' and cam control arm 57 abutting against housing 26 is sufficient to resist the downward movement of cam 38 under the influence of the spring 42. This downward movement is further resisted by cam control arm 57 resting on top of ramp member 56. The cam member 38 remains in this position indefinitely, thus allowing the needle guard 24 to partially expose needle 18 for filling syringe 14.

Figure 3:
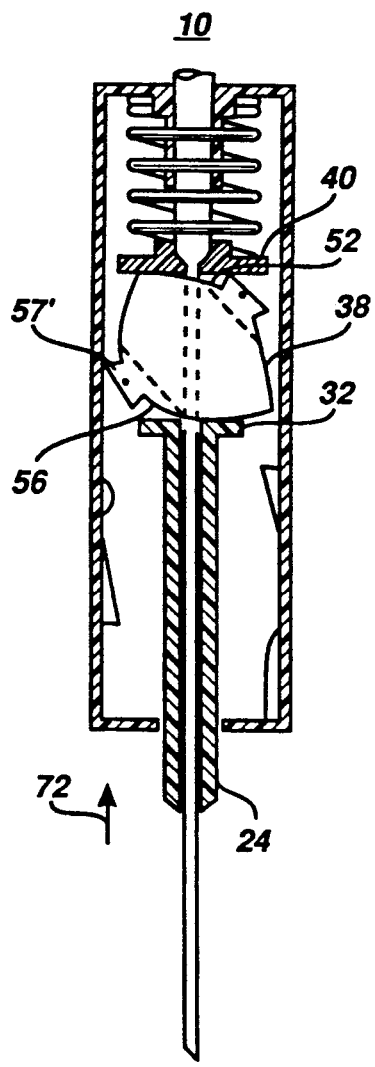
FIG. 3 is a cross-sectional view taken along section A-A', wherein the apparatus of the present invention has been triggered for an injection.
Figure 8:
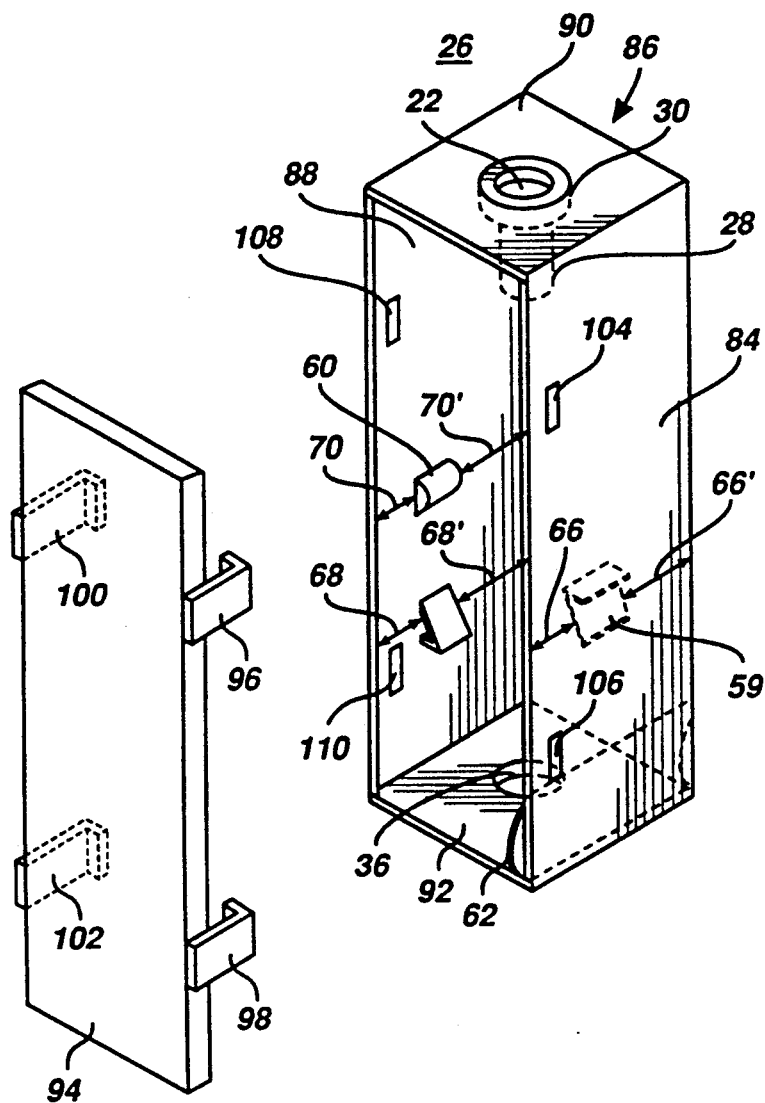
FIG. 8 is a view in perspective of the housing of the apparatus of the present invention.

Referring now to FIGS. 3 and 8, in the process of performing an injection the needle 18 is inserted into the flesh of a subject (phantom lines). The insertion process creates an upward force against needle guard 24 (represented by directional arrow 72) which, in turn, urges cam 38 upwardly, thus raising and releasing cam control arm 57' from resting engagement with trigger shoulder 60. The cam surfaces 52-52', 56-56' rotate against spacer element 40 and disk-shaped flange 32, respectively, to the intermediate position shown in FIG. 3. The rotational movement of cam 38 is induced due to the compressive forces of spring biased spacer 40 and disk-shaped member 32 compressing against cam surfaces 52-52', 56-56', respectively as well as the offset angular alignment of cam 38 while in the initial resting position.

Figure 4:
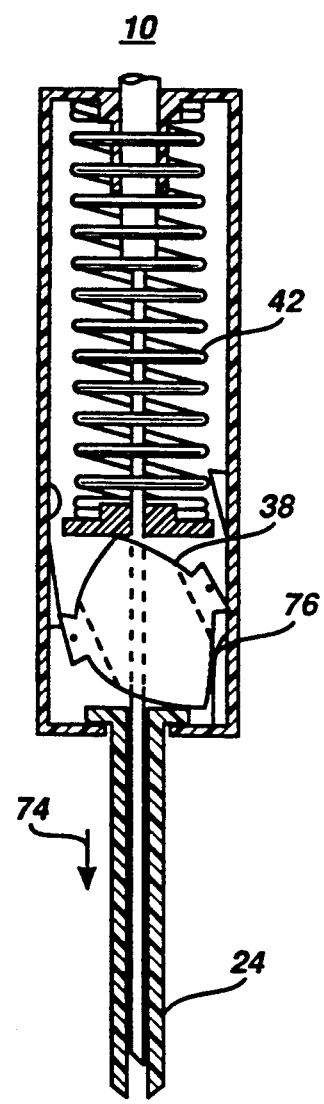
FIG. 4 is a cross-sectional view taken along section A-A', wherein the apparatus of the present invention is withdrawn from a patient and the needle guard moves toward its locked position.

As shown in FIG. 4 and 8, as the needle 18 is withdrawn from the subject, the spring 42 urges spacer 40 and cam 38 forwardly and needle guard 24 outwardly (as indicated by directional arrow 74), so that the needle 18 is completely encased by the needle guard 24 as it is withdrawn from the subject. Specifically, as cam 38 moves toward the endwall 37, cam plates 46-46' pass through gaps 66-66', 68-68' and 70-70', respectively, wherein cam plates 46-46' ultimately engage resting shoulder 62. As spring 42 and spacer 40 urge cam 38 toward end wall 37, cam 38 pivots against resting shoulder 62 at pivot point 76, thus forcing cam control arm 57' over ramp member 58.

The final locked position of apparatus 10 is shown in FIG. 5. As the cam control arm 57' is urged past ramp member 58 and an increasing rotational moment is generated about pivot point 76, cam control arm 57' travels past ramp member 58, thus snapping into position under the ramp member 58 and locking cam member 38 in its final position. This in turn locks needle guard 24 in the fully extended, protective position. In the locked position, cam member 38 is firmly held in place by cam control arm 57' locking under ramp member 58, by cam surfaces 54-54' abutting against resting shoulder 62 and by the downward force exerted by spring 42 and spacer element against cam surfaces 52-52'. Once locked, the needle guard 24 cannot be accidentally released, thereby providing a fail-safe protection against accidental exposure of needle 18.

The apparatus 10 is designed for ease of manufacture, and requires a minimum of moving parts. The components of apparatus 10 are all readily fabricated of easily obtainable materials. The housing 26, needle guard 24, cam 38 and the spacer 40 are preferably fabricated from molded nylon or other plastic materials, and the spring 42 may be manufactured from conventional stainless steel.

The cam 38 is preferably molded as a two-piece assembly as shown in FIG. 6. The first piece comprises cam plate 46, spacer walls 48, 48' and cam control arms 57-57'. The second piece of the assembly comprises cam plate 46'. The respective pieces of cam 38 may be joined with studs 78-78' which cooperatively engage annular bores 80-80' (FIG. 6). The junction between studs 78-78' and annular bores 80-80' may be secured by a conventional adhesive, by a frictional engagement, or by a conventional plastic welding process. In the alternative, cam member 38 may be molded as a one-piece unit, although this may significantly add to the expense of manufacturing cam 38. The specific length of the respective cam surfaces is not critical and are adaptable to virtually any size housing. Generally, cam surfaces 52-52' and 54-54' are generally curvilinear and of equal length. Cam control surfaces 56-56' are generally curvilinear and longer than cam control surfaces 52-52' and 54-54', respectively and cam control surfaces 50-50' are generally curvilinear and shorter than cam control surfaces 52-52', and 54-54', respectively.

Figure 7:
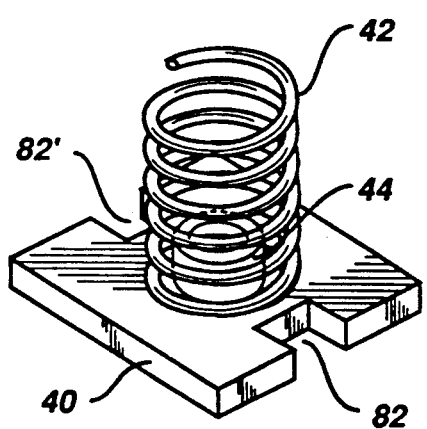
FIG. 7 is a view in perspective of the spacer member shown in cross-sectional form in FIGS. 2-5.

The spacer element 40 is generally rectangular having a perimeter dimension which is complementary with respect to the internal dimension of housing 26, so that spacer 40 element may move longitudinally within housing 26. The spacer member 40 further includes opposing notches 82-82' which permit spacer 40 to move freely past the ramp members 58, 59 and trigger shoulder 60, as it traverses the internal portion of housing 26 (FIG. 7). The spacer member 40 further includes an integral cylindrical retaining post 44 for receiving one end of spring 42. Similarly, the open ends 53-53' (FIG. 6) of cam 38 permit cam plates 52-52' to pass through gaps 66-66', 68-68' and 70-70' (FIG. 8) once cam 38 is released from its resting position and has rotated to the injection position shown in FIG. 7.

The housing 26 is preferably constructed as a two-piece molded assembly as shown in FIG. 8. In the preferred practice of the present invention, the housing 26 is formed with a square or rectangular cross-section to provide apparatus 10 with a distinctive appearance. The housing 26 includes a plurality of side walls 84, 86, and 88 which are terminated by the end walls 35, 37. End wall 35 provides a support surface for inwardly extending cylindrical wall 28 and stepped portion 30. End wall 37 includes annular orifice 36 which receives needle guard 24. Side wall 84 provides a support surface for ramp member 59 and resting shoulder 62. Side wall 88 provides a support surface for ramp member 58 and trigger shoulder 60. Housing 26 further includes side wall 94 which is configured with a plurality of inwardly biased flanged coupling arms 96, 98, 100 and 102, which engage complementary apertures 104, 106, 108 and 110 for permanently securing side wall 94 to housing 26. During manufacture, side wall 94 is manufactured as a separate member to facilitate the installation of components within housing 26. Once the spring 42, spacer 40, cam 38 and needle guard 24 have been assembled in housing 26, side wall 94 is attached to the remainder of housing 26 to complete the assembly of apparatus 10. Once side wall 94 is attached to housing 26, the inward biasing of flanged coupling arms 96-102 maintains side wall 94 in tight engagement with housing 26.

Figure 9A:
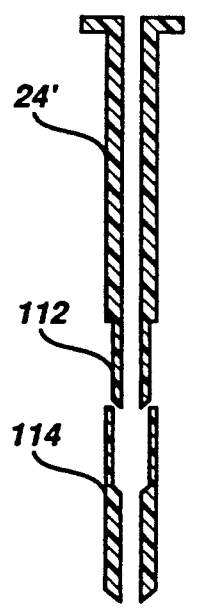
FIGS. 9A and 9B are cross-sectional views of a needle guard extension accessory and a needle guard cover adapted for use with the present invention.
Figure 9B:
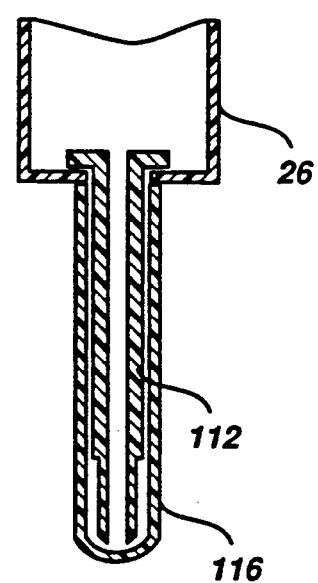

Referring now to FIG. 9A, an alternate needle guard 24' for use with the apparatus 10 is shown in cross-sectional form. The needle guard 24' includes a stepped, reduced radius, portion 112 adapted to frictionally engage a complementary extension member 114. The extension member 114 may be disposed in a variety of lengths to accommodate needles of virtually any length. In addition, as shown in FIG. 9B, a needle guard cover 116 may be provided to protect the needle guard 112 during shipping and storage.

In summary, an improved apparatus for the safe use and disposal of syringes has been described. In view of the foregoing, other uses and modifications of the present invention will be readily apparent to persons of ordinary skill. All of such uses and modifications are intended to fall within the scope of the appended claims.

I claim:

1. An improved apparatus for the safe use and disposal of syringes, said apparatus comprising;
    a housing having a plurality of side walls and first and second end walls, wherein said plurality of side walls include cam control surfaces disposed on an interior surface thereof, said first end wall including means for receiving the needle assembly of a syringe having a needle and said second end wall having an aperture aligned with said means for receiving;

a needle guard slidably disposed within the aperture of said second end wall, said needle guard having a longitudinal channel for receiving said needle, said needle guard further including a disk-like flange for limiting the movement of said needle guard within said housing;

a rotable cam disposed within said housing, said rotable cam including a plurality of cam arms responsive to said cam control surfaces, said cam further including a first and second pair of cam surfaces, said first pair of cam surfaces cooperatively disposed with respect to said disk-like flange;

a spacer member slidable disposed within said housing said spacer member including a plurality of notches aligned with said cam control surfaces which permit the movement of said spacer member over said cam control surfaces, said spacer member disposed in cooperative engagement with said second pair of cam surfaces; and spring biasing means disposed within said housing for urging said spacer member and said rotable cam in a direction opposing said first end wall.

2. The apparatus of claim 1, wherein said cam control surfaces include an upwardly directed ramp surface and a resting shoulder disposed along one of said side walls and a downwardly directed ramp surface and a trigger shoulder disposed along an opposite sidewall.

3. The apparatus of claim 1, wherein said cam member is movable between initial, injecting, withdrawing and locked positions wherein in said initial position, said cam control arms engage said upwardly directed ramp surface and said trigger shoulder so that said needle guard is slidable to expose said needle for filling said syringe, wherein in said injecting position said cam arms are released from said upwardly directed ramp surface and said trigger shoulder to compress said first and second pair of cam surfaces between said spacer member and said disk-like flange, to permit said needle guard to slide inwardly within said housing, and wherein in said withdrawing position, said cam member moves outwardly within said housing to force said needle guard over said needle as it is withdrawn in response to forces generated by said spring, and wherein in said locked position, said cam control arms engage said downwardly directed ramp surface and said resting shoulder to lock said needle guard in a fully extended position wherein said needle is completely contained within said longitudinal channel.

4. A method for the safe use and disposal of a syringe, said method comprising the steps of:

covering the needle portion of a syringe with a needle guard, said needle guard slidable between retracted, partially retracted holdable and extended lockable positions, said needle guard coupled to a biased, internal rotatable cam member, said cam member being adapted to urge said needle guard over said needle portion;

sliding said needle guard to said partially retracted position, fixedly holding said biased cam member in a filling position to permit filling of said syringe prior to injecting a subject;

sliding said needle guard to said retracted position in opposition to said biased cam member while injecting a subject;

sliding said needle guard over said needle portion as it is withdrawn from said subject in response to said biased cam member; and locking said needle guard in said fully extended position upon completely withdrawing said needle portion from said subject.

5. The method of claim 4, further including the steps of releasing said biased cam member from said filling position upon the initiation of injecting a subject.

6. An improved apparatus for the safe use and disposal of a syringe, said apparatus comprising:

a needle guard for covering the needle portion of a syringe, said needle guard slidable between retracted and extended lockable positions;

biasing means to urge said needle guard over said needle portion wherein said needle guard is adapted to slide to said retracted position in opposition to said biasing means for injecting a subject and further wherein said needle guard is adapted to slide over said needle portion as it is withdrawn from a subject in response to said biasing means;

an internal cam means for fixedly holding said biasing means in a filling position which permits movement of said needle guard to a partially exposed position to permit filling of said syringe prior to injecting a subject, and means for releasing said biasing means from said filling position upon the initiation of injecting a subject; and means for locking said needle guard in said fully extended position upon completely withdrawing said needle portion from said subject.

7. Apparatus for the safe use and disposal of a syringe having a syringe body and a needle with a tip, said apparatus comprising:

a cam housing portion having a first end wall and a second end wall with an opening for the passage of said needle;

a needle guard having an internal channel for said needle and slidably disposed in said opening and over said needle, said needle guard having means for preventing removal of said needle guard through said opening;

a cam member rotatably disposed within said cam housing, said cam member having cam surfaces and engagement portions;

said cam housing having interior cam control surfaces for engaging said engagement portions of said cam member;

biasing means having a biasing surface adapted to engage said cam member and to urge said cam member toward said needle guard and said second end wall, said needle guard when positioned for an injection being urged through said opening and toward said first end wall to expose said needle, said cam member rotating about at least one cam surface such that at least one engagement portion is removed from engagement with at least one cam control surface, and after injection release of said needle guard permitting said biasing means to urge said cam member and said needle guard toward said second end wall, and further rotating said cam member about at least one cam surface such that at least one engagement portion engages at least one cam control surface to lock said needle guard in a position enclosing said needle.

* * * * *